(12) United States Patent
Schmidt et al.

(10) Patent No.: US 9,254,110 B2
(45) Date of Patent: Feb. 9, 2016

(54) AUTOMATICALLY OBTAINING OPTIMIZED OUTPUT DATA

(71) Applicant: Siemens Aktiengesellschaft, Munich (DE)

(72) Inventors: Bernhard Schmidt, Fuerth (DE); Martin Sedlmair, Zirndorf (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 86 days.

(21) Appl. No.: 14/244,041

(22) Filed: Apr. 3, 2014

(65) Prior Publication Data

US 2014/0307847 A1    Oct. 16, 2014

(30) Foreign Application Priority Data

Apr. 11, 2013 (DE) .......................... 10 2013 206 415

(51) Int. Cl.
*A61B 6/00* (2006.01)
*A61B 6/03* (2006.01)

(52) U.S. Cl.
CPC ................ *A61B 6/482* (2013.01); *A61B 6/032* (2013.01); *A61B 6/5205* (2013.01); *A61B 6/405* (2013.01)

(58) Field of Classification Search
CPC ...... A61B 6/482; A61B 6/032; A61B 6/5205; A61B 6/405
USPC .................................. 382/128–132; 378/4–20
See application file for complete search history.

(56) References Cited

PUBLICATIONS

David R. Holmes et al., Evaluation of non-linear blending in dual-energy computed tomography, Eur J Radiol. Dec. 2008, 68(3), pp. 409-412.
Alvin C. Silva et al., Dual-Energy (Spectral) CT: Applications in Abdominal Imaging, RadioGraphics 2011, 31, pp. 1031-1046.
Eusemann Christian et al; "Dual Energy CT—How to best blend both energies in one fused image?"; Proc. of SPIE; vol. 6918; pp. 691803-1-691803-8; DOI:10.1117/12.773095; 2008.
German Office for DE102013206415.2 dated Dec. 3, 2013.
German Priority Document German Application 10 2013206415.2 filed Apr. 11, 2013.

*Primary Examiner* — Courtney Thomas
(74) *Attorney, Agent, or Firm* — Harness, Dickey & Pierce, P.L.C.

(57) ABSTRACT

A method and a system are disclosed for obtaining image data from inside an examination object from images of a computed tomograph. In an embodiment, the method includes accepting first measurement data of the examination object, acquired based on x-ray radiation of a first energy, and second measurement data of the examination object, acquired based on x-ray radiation of a second energy differing from the first energy; setting an optimized output of target image points on the basis of the first and second measurement data at the respective target image points, each as a function of local optimization parameter values of the target image points determined locally from the first and second measurement data in the area of the target image points, while deriving image point reproduction parameter values representing the optimized output; and determining the output data based on optimized output of the target image points.

18 Claims, 4 Drawing Sheets

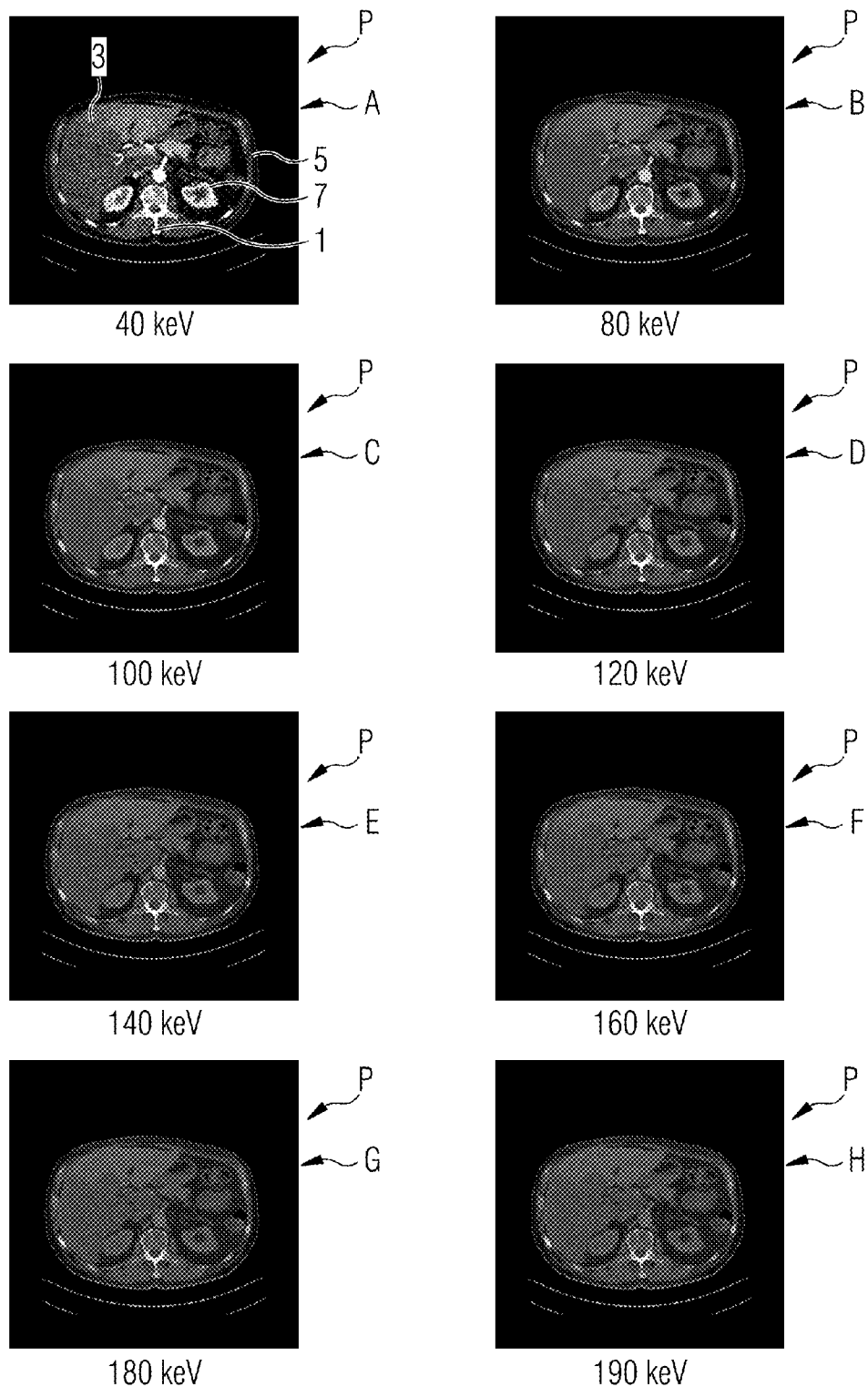

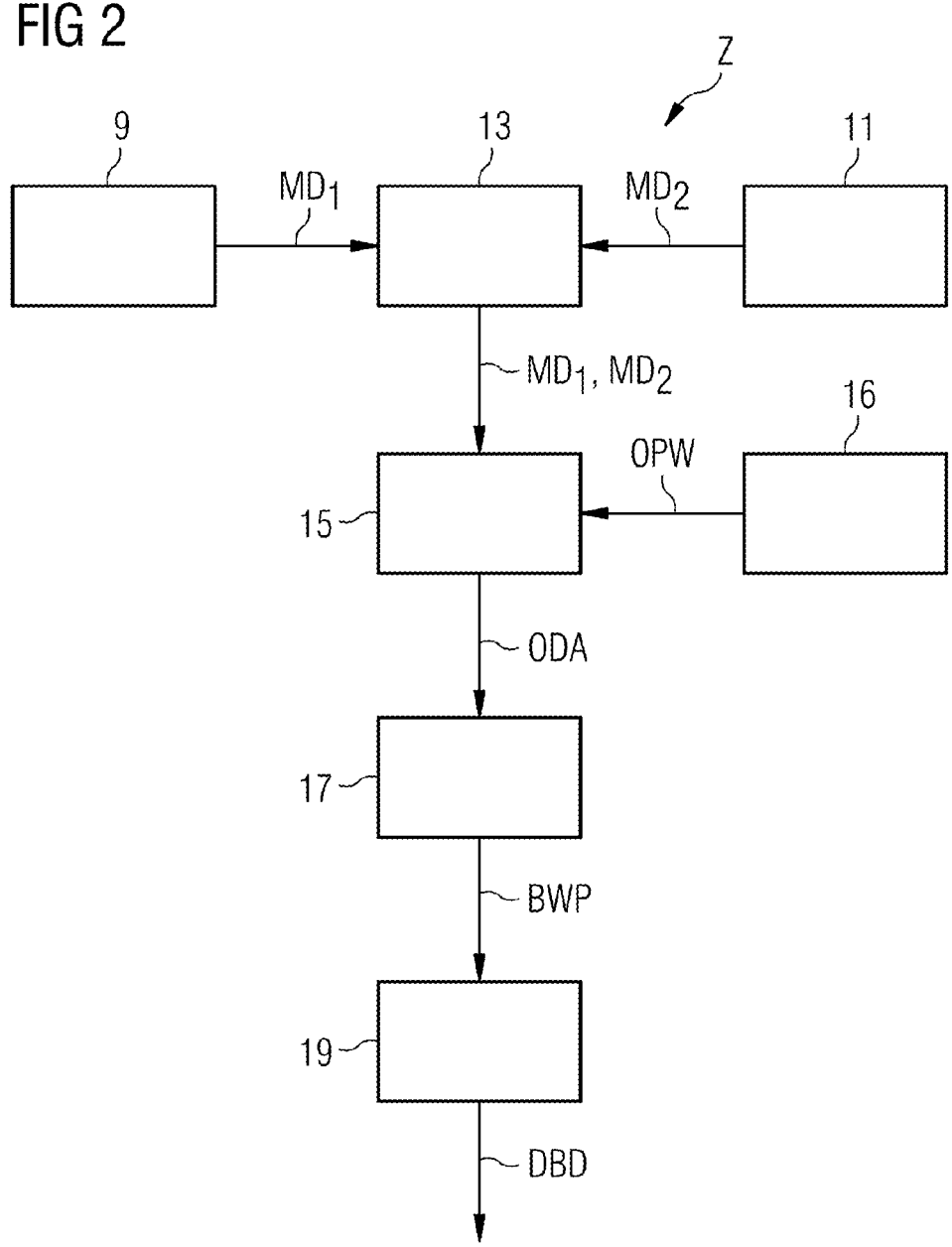

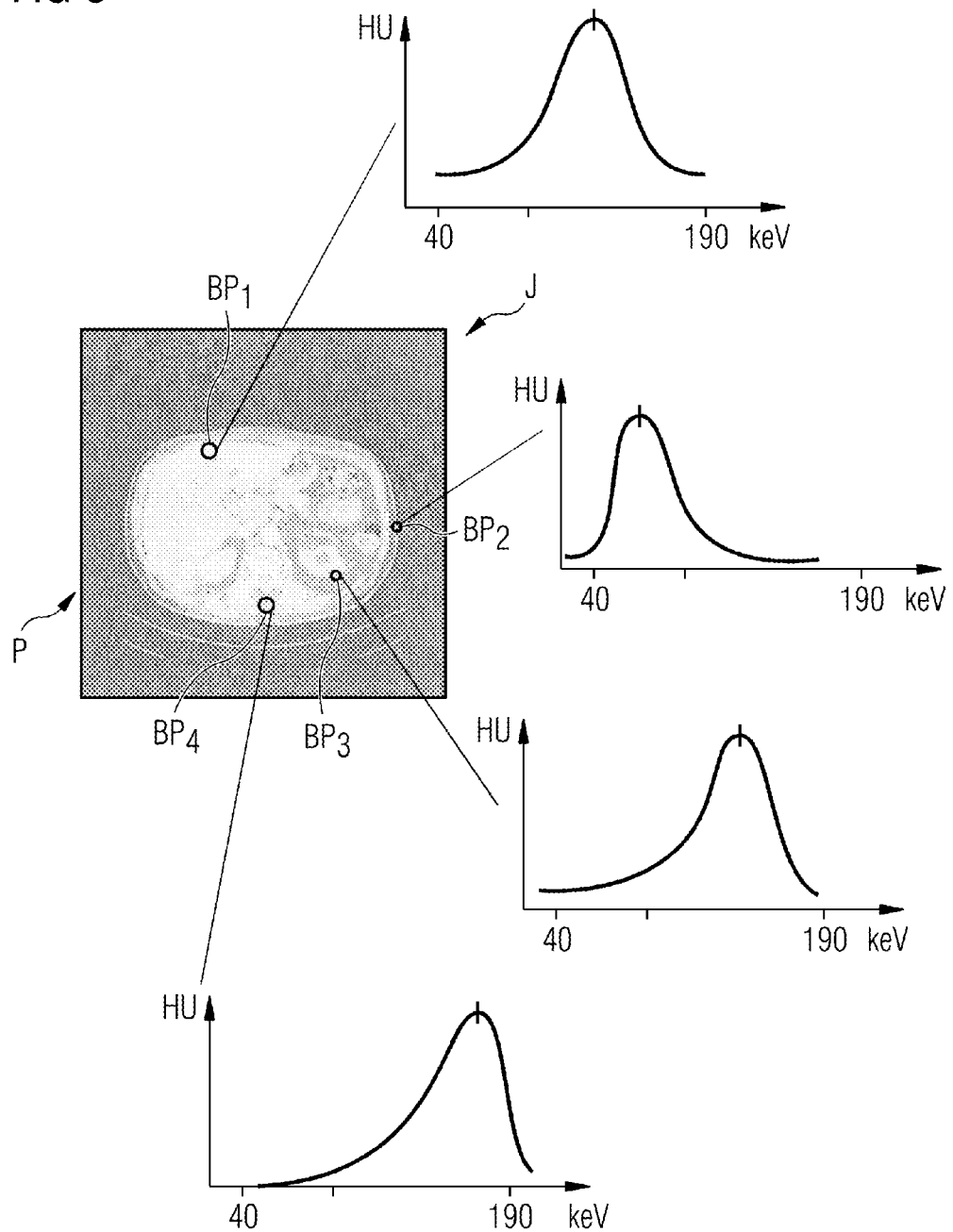

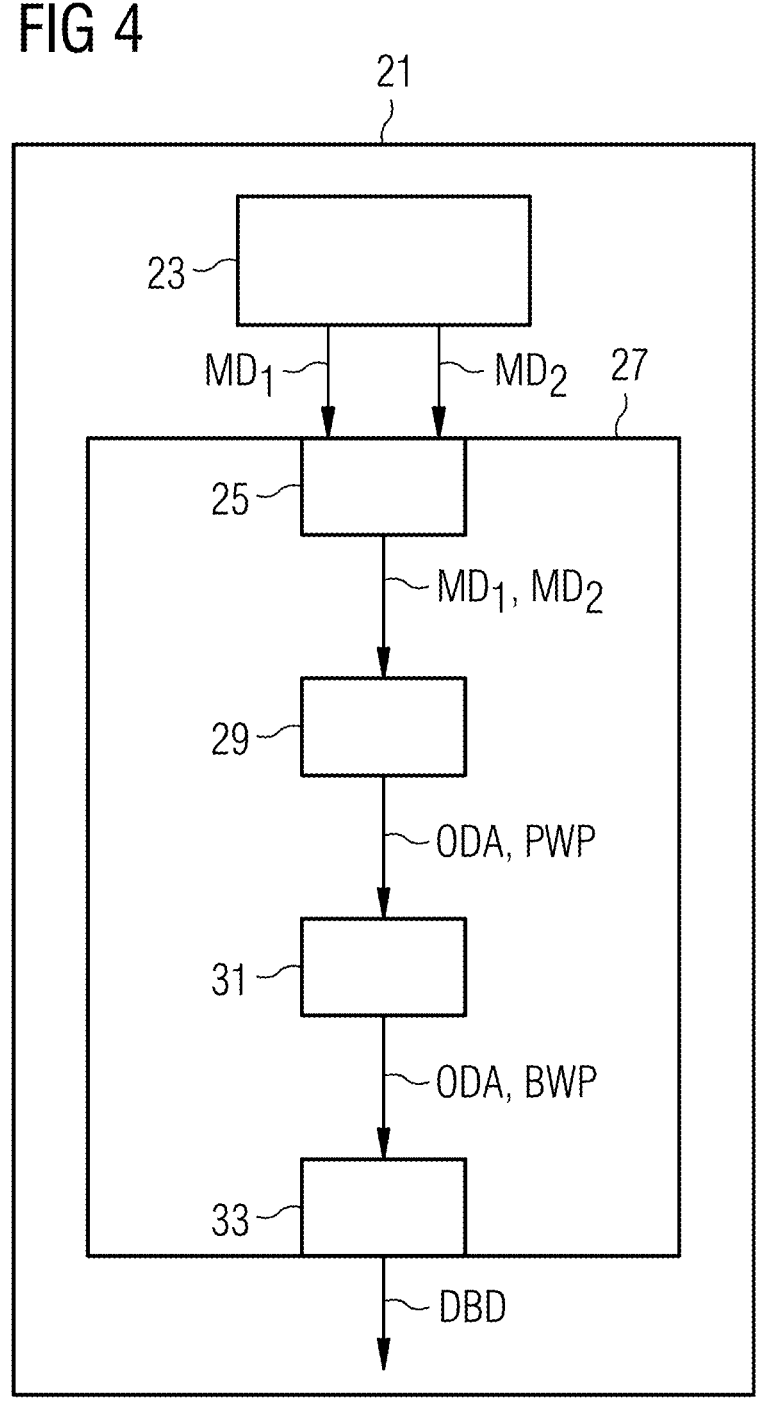

AUTOMATICALLY OBTAINING OPTIMIZED OUTPUT DATA

PRIORITY STATEMENT

The present application hereby claims priority under 35 U.S.C. §119 to German patent application number DE 102013206415.2 filed Apr. 11, 2013, the entire contents of which are hereby incorporated herein by reference.

FIELD

At least one embodiment of the present invention generally relates to a method for automatically obtaining optimized output data from inside an examination object from images of the computed tomograph. It also generally relates to an image data acquisition system for obtaining optimized output data from inside an examination object from images of the computed tomograph.

BACKGROUND

In computed tomography, for improved material differentiation in a body to be imaged what is known as the multi-spectrum method (also referred to as the multiple energy method) or the two-spectra method (dual-energy method) is often applied. In such methods (approximately) the same point of the body is irradiated from (approximately) the same direction simultaneously or in turn by x-rays of different energies—in the multiple energy method this is generally a plurality of different x-rays (spectra), in the dual-energy method (a subordinate generic form of the multiple energy method) it is precisely two.

With multiple energy methods at least two different x-ray projections are thus created which result from the different typical energies. This enables the absorption characteristic of a body, specifically of an organic tissue or structures supported within said tissue, to be taken into account as well during the imaging: this absorption characteristic is namely decisively dependent on the energy of the x-ray radiation. Usually on the basis of the x-ray projection data from x-ray radiation with low typical energy a low-energy image and on the basis of x-ray projection data from x-ray radiation with high typical energy a high-energy image is reconstructed. These two images can then be combined with one another in order for example to create from them a soft tissue image or a bone image of a patient. With the aid of the multiple energy method a better discrimination of different materials within an area of the body to be imaged is possible in this way, such as the differentiation between bone tissue and contrast media in an examination area.

Thus a separate so-called single-energy image stack is created or computed from each acquisition with one energy in each case, which can be provided both singly (as already described) or in a combined image stack (with the respective other image stack(s)) for optimized output. In the latter case it is important for the output parameter of the combined image stack to be selected so that the user can be offered an optimized increase in their knowledge during viewing. An output optimization in this sense takes account for example of the so-called contrast-noise ratio (CNR), in which a maximum possible contrast in relation to a minimum possible noise is achieved in the combined image stack output.

Two basically different combination methods exist at present for combining a number of single-energy image stacks into a combined image stack, namely what is referred to as the optimum contrast method and another method in which a mono-energetic image stack is created.

The optimum contrast method is described for example in the article by Holmes, David, et al.: "Evaluation of non-linear blending in dual-energy computed tomography". Eur J Radiol. 2008 December, 68(3), Pages 409 to 413, the entire contents of which are incorporated herein by reference. In this method an optimum ratio is computed with the aid of a non-linear algorithm from a low-energy and a high-energy portion of two dual-energy image stacks and the two image stacks are blended with one another, i.e. mixed. This involves a so-called sigmoidal blending, i.e. that the respectively determined optimum portions of the two image stacks result in the mixed image stack in a non-linear, namely sigmoidal manner.

The creation of a mono-energetic image stack is described for example in the article by Silva, Alvin et al.: "Dual-Energy (Spectral) CT: Applications in Abdominal Imaging". Radio-Graphics 2011, 31, pages 1031 to 1046, the entire contents of which are incorporated herein by reference. In this method, starting from the two (or more) image stacks presented created by measurement a further, virtual image stack is created which is based on an assumed (third) energy, which is usually different from the number of energies during image acquisition. The third energy assumed in this case is for its part selected so that an output optimization in the manner mentioned above will be obtained.

With the aid of the method presented here an output optimization can be obtained over an entire combined image stack, i.e. that the aim is always to optimize the output of the combined image stack as a function of a specific output interest. Specific image areas (such as specific organs or structures) are necessarily presented especially well while the imagability of other image areas also necessarily suffers from this approach.

SUMMARY

At least one embodiment of the invention is directed to further optimizing the image output of measurement data obtained in a multiple-energy method. This relates especially preferably to the optimization of the detectability of different structures within the body of the examination object.

A method and a system are disclosed.

A method of at least one embodiment comprises at least the following:

a) Acceptance of first measurement data of the examination object which was acquired on the basis of x-ray radiation of a first energy, and of second measurement data of the examination object which was acquired on the basis of x-ray radiation of a second energy differing from the first energy, b) Setting an optimized output of target image points on the basis of the first and second measurement data at the respective target image points as a function in each case of local optimization parameter values of the target image points, which are determined locally in each case from the first and second measurement data in the area of the target image points, with derivations of image point reproduction parameter values which represent the optimized output of the target image points, and c) Determining the output data on the basis of the optimized output of the target image points.

A system is disclosed in at least one embodiment for obtaining image data of the aforementioned type comprises at least the following:

An input interface (which can also include a plurality, for example two individual input interfaces for example for separate data transfer of the first and second measurement data)

for accepting first measurement data of the examination object, which was acquired on the basis of x-ray radiation of a first energy, and of second measurement data of the examination object which was acquired on the basis of x-ray radiation of a second energy different from the first energy, A setting and derivation unit which during operation derives an optimized output of target image points based on the first and the second measurement data as a function of local optimization parameter values of the target image points, which are determined locally in each case from the first and second measurement data in the area of the target image points and which in operation derives image point reproduction parameter values which represent the optimized output of the target image points, and A determination unit which is embodied so that it determines the output data on the basis of the optimized output of the target image points.

The interfaces (those mentioned and if necessary others) do not necessarily have to be embodied as hardware components, but can also be realized as software modules, for example when the image data can be transferred from another component already realized on the same device, such as an image reconstruction facility or the like for example, or only has to be transferred to another component by software. Likewise the interfaces can include hardware and software components, such as for example a standard hardware interface which is specifically configured by software for its actual intended purpose. In addition a number of interfaces can also be combined into one common interface, for example an input/output interface.

At least one embodiment of the invention therefore also includes a computer program product which is able to be loaded directly into a processor of a programmable system for obtaining image data, with program code means for executing all steps of embodiments of the inventive method when the program product is executed on the system for obtaining image data.

The invention also includes a computed tomograph with an acquisition unit and an inventive system for obtaining image data.

BRIEF DESCRIPTION OF THE DRAWINGS

The invention will be explained below once again in greater detail with reference to the enclosed figures on the basis of example embodiments. The same components are provided with identical reference numbers here in the various figures. In the figures:

FIG. 1 shows eight output images from computed tomography recordings with different energies in accordance with the prior art, FIG. 2 shows a schematic block diagram of an example embodiment of an inventive method, FIG. 3 shows a computed tomography acquired image with assigned local measurement curves of the Hounsfield values as a function of the acquisition energy, and FIG. 4 shows a schematic block diagram of an example embodiment of an inventive computed tomograph with an example embodiment of an inventive system for obtaining image data.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Before discussing example embodiments in more detail, it is noted that some example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Methods discussed below, some of which are illustrated by the flow charts, may be implemented by hardware, software, firmware, middleware, microcode, hardware description languages, or any combination thereof. When implemented in software, firmware, middleware or microcode, the program code or code segments to perform the necessary tasks will be stored in a machine or computer readable medium such as a storage medium or non-transitory computer readable medium. A processor(s) will perform the necessary tasks.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

In the following description, illustrative embodiments may be described with reference to acts and symbolic representations of operations (e.g., in the form of flowcharts) that may be implemented as program modules or functional processes include routines, programs, objects, components, data structures, etc., that perform particular tasks or implement particular abstract data types and may be implemented using existing hardware at existing network elements. Such existing hardware may include one or more Central Processing Units (CPUs), digital signal processors (DSPs), application-specific-integrated-circuits, field programmable gate arrays (FPGAs) computers or the like.

Note also that the software implemented aspects of the example embodiments may be typically encoded on some form of program storage medium or implemented over some type of transmission medium. The program storage medium (e.g., non-transitory storage medium) may be magnetic (e.g., a floppy disk or a hard drive) or optical (e.g., a compact disk read only memory, or "CD ROM"), and may be read only or random access. Similarly, the transmission medium may be twisted wire pairs, coaxial cable, optical fiber, or some other suitable transmission medium known to the art. The example embodiments not limited by these aspects of any given implementation.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

A method of at least one embodiment comprises at least the following:

a) Acceptance of first measurement data of the examination object which was acquired on the basis of x-ray radiation of a first energy, and of second measurement data of the examination object which was acquired on the basis of x-ray radiation of a second energy differing from the first energy, b) Setting an optimized output of target image points on the basis of the first and second measurement data at the respective target image points as a function in each case of local optimization parameter values of the target image points, which are determined locally in each case from the first and second measurement data in the area of the target image points, with derivations of image point reproduction parameter values which represent the optimized output of the target image points, and c) Determining the output data on the basis of the optimized output of the target image points.

The acceptance of the first and second measurement data can include the generation of this measurement data within the framework of an image acquisition, but it can also be undertaken subsequent to such an image acquisition and therefore includes a straightforward measurement data transfer, from a storage medium for example. "Measurement data" within the framework of this description is both projection data, i.e. raw data obtained from an image acquisition of the computed tomograph, and also reconstructed image data. If raw data is accepted as measurement data this raw data will be reconstructed during the course of the inventive method into reconstructed image data.

The energetic characteristic of the energy spectrum of the respective x-ray radiation which is usually conventionally equated with the term energy is understood—below as well—as energy or also as typical energy of the x-ray radiation. If this document refers to a first and a second energy, this definition of typical energy will always be used as a basis. A variation of the energy of an x-ray radiation consequently means a shifting of the x-ray spectrum to lower or higher energy values, i.e. specifically of the average energy or of the highest energy values achieved. The typical energy is mostly specified in the form of a specification of the acceleration voltage of the x-ray source, which usually lies with dual-energy measurements or systems at values of 140 kV and 80 kV.

Both a sufficiently known x-ray tube which rotates on a side of the gantry of the computed tomograph opposite to the detector arrangement and also an arrangement in which an electron beam is directed from outside the gantry circulating to focal points within the gantry can be used as an x-ray source. The x-ray radiation is then created at these focal points.

In step b), after the measurement data has been accepted, an optimized output of target image points is then set. It is precisely here that the fundamental difference to the prior art lies, namely in that, instead of a general output adaptation in an entire image stack, individual image points are now adapted in their output. A local output adaptation is thus involved, namely an image point-based adaptation. Image points in this case can be understood as individual pixels or voxels within the measurement data or within the body of the examination object to be imaged. The "target image points" relate to a location in the examination object. It can be assumed for each such location that both a measured value is present in the first image data and also in the second image data from a number of projections. On the basis of these measured values the target image point will be determined and defined within the measurement data itself. Each target image point therefore has a correspondence as pixel or voxel in the resulting output data; the totality of all target image points forms the totality of all pixels or voxels in the output data.

The result achieved by the image point-oriented adaptation of the output is that for each image point (and if necessary its immediate environment) an optimum is achieved in accordance with the underlying optimization parameter value. Although through this method the reproduction of the measurement data can give the impression of being somewhat falsified, this effect is by far compensated for by the benefit of a better detectability of structures in the output data. A user can namely now significantly more clearly detect even small peculiarities in significantly enlarged image areas. This increases the benefit for the user significantly.

At least one embodiment of the invention thus departs from the "General" setting of output parameters and turns instead to a setting in the micro area of the output data. A significant refinement of the overall output is achieved by this.

The determination in step c) can follow on from a presentation of the output data, such as a display or a printout, however can also be a simple passing on of the output data to other modalities and/or a storage with the purpose of archiving and/or passing on the data.

A system is disclosed in at least one embodiment for obtaining image data of the aforementioned type comprises at least the following:

An input interface (which can also include a plurality, for example two individual input interfaces for example for separate data transfer of the first and second measurement data) for accepting first measurement data of the examination object, which was acquired on the basis of x-ray radiation of a first energy, and of second measurement data of the examination object which was acquired on the basis of x-ray radiation of a second energy different from the first energy, A setting and derivation unit which during operation derives an optimized output of target image points based on the first and the second measurement data as a function of local optimization parameter values of the target image points, which are determined locally in each case from the first and second measurement data in the area of the target image points and which in operation derives image point reproduction parameter values which represent the optimized output of the target image points, and A determination unit which is embodied so that it determines the output data on the basis of the optimized output of the target image points.

Preferably the system for obtaining image data is embodied so that it carries out an inventive method fully automatically, i.e. independently. It can however also operate semi-automatically, i.e. be supplied with the necessary additional information by additional input from outside, for example from further logic units which are possibly linked to databases, or through manual input of an operator. This input can especially relate to other information about the body which has been scanned during image acquisition. For example basic data for a person being scanned in the computed tomograph can be fed in via a patient information storage system.

Overall a majority of the components for realizing the system for obtaining image data in the inventive manner, especially the setting and derivation unit, can be realized entirely or in part in the form of software modules on a processor.

The interfaces (those mentioned and if necessary others) do not necessarily have to be embodied as hardware components, but can also be realized as software modules, for example when the image data can be transferred from another component already realized on the same device, such as an image reconstruction facility or the like for example, or only has to be transferred to another component by software. Likewise the interfaces can include hardware and software components, such as for example a standard hardware interface which is specifically configured by software for its actual intended purpose. In addition a number of interfaces can also be combined into one common interface, for example an input/output interface.

At least one embodiment of the invention therefore also includes a computer program product which is able to be loaded directly into a processor of a programmable system for obtaining image data, with program code means for executing all steps of embodiments of the inventive method when the program product is executed on the system for obtaining image data.

The invention also includes a computed tomograph with an acquisition unit and an inventive system for obtaining image data.

Further especially advantageous embodiments and developments of the invention emerge from the dependent claims and from the description given below. In such cases the system for obtaining image data can also be developed in accordance with the dependent claims for the method.

Especially preferably the first energy is created by operation of an x-ray source with an acceleration voltage of appr. 140 kV and the second energy by operation of an x-ray source with an acceleration voltage of between appr. 80 and 100 kV. Acceleration voltages of 80 and 140 kV are typical standard values in the dual-energy method, so that possibly even a simple reprogramming of existing computed tomography systems is possible for carrying out the inventive method. In addition the best empirical values are thus also available for this energy pairing.

The output data can be optimized in accordance with different aspects. These aspects are represented in the method by the optimization parameter values taken into consideration. It is preferred in such cases that the optimization parameter values of the respective target image points include at least one of the following parameter values:

The contrast between a target image point and its immediate environment: By taking account of this optimization parameter value a local contrast variation can be achieved at the respective image point.

Image noise at the target image point and its immediate environment: By taking account of this optimization parameter value a local variation of the noise at the respective image point can be achieved.

Contrast-noise ratio (CNR) of the image point and its immediate environment: By taking account of this optimization parameter value both the contrast and also the image noise will be tailored to each other in the optimum possible way.

Output signal strength at the target image point: By taking account of this optimization parameter value the brightness can be set at the respective image point.

In this context it is to be noted that the method can also be operated simultaneously taking into consideration a number of optimization parameter values. One example is the CNR, but for example the output signal strength can also be taken into account combined with one of the other said optimization parameter values or optimization parameter value conditions formed therefrom can be optimized. Preferably optimization is undertaken over the entire measurement data based on the same optimization parameter value or values, since through this a thorough and inherently logically complete optimization takes place, which does not unnecessarily falsify the output data derived here from and thus tend to confuse rather than simplify the results of the viewing for a user. In principle however a local (i.e. image point-based) mixed optimization, i.e. possible locally taking into consideration different optimization parameter values, such as when different knowledge interests of a user play a role for different subareas of the output data. These types of phenomenon occur for example during whole-body scans as a result of accidents in which the entire body of the examination object, i.e. patient involved in the accident, has to be examined for different types of injury, such as both broken bones and also organ injuries.

In accordance with the first variant of an embodiment of the inventive method the contrast between the target image point and its immediate environment is regulated to a maximum. The contrast increased before the setting of all other optimization parameter values thus plays the decisive role here.

In accordance with the second (alternative) variant of an embodiment of the inventive method, the contrast-noise ratio of the image point and its immediate environment are regulated to a maximum. The optimum ratio between contrast and image noise before the setting of all other optimization parameter values plays the decisive role here.

In accordance with a third (likewise alternative) variant of an embodiment of the inventive method, the output signal strength at the target image point will be regulated to a maximum. Here the output signal strength (usually reproduced in Hounsfield Units—HU) before the setting of all other optimization parameter values plays the decisive role here.

In accordance with a fourth (likewise alternative) variant of an embodiment of the inventive method the image noise at the target image point and its immediate environment will be regulated to a minimum. The reduction of the image noise before the setting of all other optimization parameter values now plays the decisive role here.

All these four variants, as mentioned above, can be tuned to one another and a user-dependent weighting can be undertaken.

Basically it is possible to determine the optimization parameter values exclusively at the respective target image point itself. On the other hand, starting from the target image point, a larger-surface or larger-volume area can be investigated for the respective optimization parameter value. It is preferred that the optimization parameter values of the respective target image points are determined as a function of a parameter value determination at the respective target image point and its immediate environment. Such an immediate, i.e. near environment is especially understood as a environment of up to 5 image points, preferably of up to 3 image points, especially preferably of up to 1 image points. The result achieved by this is that, especially with an optimization based on optimization parameter values such as the contrast, the image noise or similar, environment-dependent optimization parameter values, meaningful results can be generated.

The same applies in a similar manner for the regulating in of the image reproduction parameter values. These too can be exclusively regulated at the respective target image point. On the other hand, starting from the target image point, a larger-surface or larger-volume area can be regulated in to the respective image point reproduction parameter value. But here too, for the reasons given above, it is especially preferred that the image point reproduction parameter values of the respective target image points are regulated in to the respective target image point and its immediate environment. In other words: image point reproduction parameter values of a target image point also determine the image point reproduction parameter values in its immediate environment. This does not necessarily mean that the image point reproduction parameter values must be defined the same as those of the target image point for the environment of a target image point, but merely depending on the target image point reproduction parameter value at this target image point. This produces a softer transition in the image presentation, in which no jumps that are too abrupt are to be seen in the image point reproduction parameter values, which could otherwise distort the output data too much from image point to image point and could therefore falsify it.

In principle it continues to be possible to apply step b) just for selected individual target image points in the output data; to treat these target image points for example as a type of representative for their further environment. Such representatives can especially be localized such that they represent different structures of the examination object (such as different organs and/or tissue and/or bone structures etc.). They can also be localized so that they are disposed in accordance with a predetermined regular or irregular pattern in the output data. It is preferred that the execution of the step b) is undertaken for a number, and especially preferably for all, target image points of the examination object directly adjacent to one another. This means that the examination object can be output optimized pixel-by-pixel or voxel-by-voxel in accordance with the inventive method, either area-by area or—as preferred—completely. This method of operation increases the quality with the aid of the inventive method the most.

Another possibility resides in the execution of step b) for all target image points within a previously defined representation area of the examination object. The focus here is thus on a part of the imaging of the examination object, namely preferably the part to which the knowledge interests of the user, such as an investigating doctor, apply. In particular the defined presentation area can include one or more organs and/or structures such as bones, tissues, vessels and much more to which this knowledge interest is directed.

The derivation of the respective image point reproduction parameter values can for example be undertaken in accordance with one of the following alternatives.

The first alternative includes the respective image point derivation parameter values in step b) being derived by the first and the second measurement data at the respective target image point being mixed with one another as a function of a ratio derived from an optimization parameter value present at the respective target image point. This mixing of the two items of measurement data can also be referred to as blending, as has already been described above. Thus the optimum contrast methods described above is now applied locally, related to the respective target image points and if necessary their immediate (or also further) environment. In this context the reader is referred once again to the literature reference cited above and the further information about the optimum contrast method.

The second alternative includes the respective image point reproduction parameters in step b) being determined by calculation of mono-energetic target image points in each case based on a third energy from the two measurement data with reference to an assignment database. Thus, as has likewise been described above for the prior art, a third energy is determined by simulation and used as a basis for the local image reproduction at the target image point. For this purpose there is recourse to a corresponding assignment database in which the corresponding reproduction values (specifically the HU value) are specified for particular virtual energies.

Thus local (at the target image point) virtual x-ray projection data or reconstructed image data is defined, which—derived from the first and second measurement data—represents projections or image values of (approximately) the same location of the body from (approximately) the same direction of virtual x-ray radiation emitted with a third energy. Virtual x-ray projection data can especially be determined on the basis of the methods of Alvarez and Macovski (see: Alvarez, Robert E./Albert Macovski: Energy-selective Reconstructions in X-ray Computerized Tomography. Phys. Med. Biol. 1976, Vol. 21, No. 5, Pages 733 to 744 and also Alvarez, Robert/Edward Seppi: A Comparison of Noise and Dose in Conventional and Energy Selective Computed Tomography. IEEE Transactions on Nuclear Science, Vol. NS-26, No. 2, April 1979, pages 2853 to 2856, the entire contents of each of which are hereby incorporated herein by reference.), i.e. derived from first and second measurement data in the former first and second x-ray projection data. In such cases a material decomposition of the irradiated structure is carried out from the two x-ray projection data of the two x-ray beams of different energy. Their respective surface densities are derived from the materials derived from the decomposition from which, in the reverse of this procedure, the attenuation coefficient for x-ray radiation of practically any given energy is able to be calculated. Based on the knowledge of these absorption properties for a (virtual) third energy, the x-ray projection data corresponding to the energy can thus be derived virtually.

In addition, an embodiment of the inventive method can be developed by the respective image point reproduction parameter values being derived as a function of knowledge interest-oriented parameter specifications for the examination object and/or for a target region of the examination object. As well as the optimization parameter values mentioned above, additional (specifically subordinate) parameter values can also thus be taken into consideration. Such parameters can for example be produced from the requirements of a diagnostic specialist using the output data (i.e. the request of the output data) and/or be related to a specific structure to be examined, such as specific organs or a number of organs, tissue, bones, vessels and much more. Good detectability of different organs often requires a very different reproduction: thus for example the air-filled lungs can be presented better in one type of presentation than an approximately water-filled blood vessel.

These parameter specifications of the additional parameter values are especially preferably obtained by a user. In such cases, before the preferably exclusively automatic, pure algorithm-based inventive method is carried out, the user gives his or her input, on the basis of which the method is then carried out. The user input can also be undertaken by an explicit request. In particular the method is therefore executed fully automatically as from its step b).

FIG. 1 shows eight output images A, B, C, D, E, F, G, H of the same slice through the same patient P, acquired at different energies, namely at 40 keV for output image A, at 80 keV for output image B, at 100 keV for output image C, at 120 keV for output image D, at 140 keV for output image E, at 160 keV for output image F, at 180 keV for output image G and at 190 keV for output image H.

In the output images A, B, C, D, E, F, G, H the spinal column 1, i.e. bone, the liver 3, fatty tissue 5 and the kidneys 7 can be seen, but with different acquisition energies with different clarity in each case. Thus for example the spinal column 1 can be seen especially well in the first output image A with the lowest acquisition energy level. The same applies for the kidneys 7. In the liver 3 on the other hand a relatively high image noise is to be seen in the output image A, so that the liver 3 can be seen at its most uncorrupted in the last output image H. The same applies for fatty tissue 5.

The output images A, B, C, D, E, F, G, H can both be acquired in separate recordings in each case with different energies or starting from at least two recordings with different energies, output images can also be created artificially by computation based on stored database values. Typically an image acquisition is carried out at 80 keV and 140 keV and the output images A, C, E, F, G, H can be derived from this. These virtual derivations for the respective underlying energies also serve for example to make specific target structures such as the organs, tissue and bones mentioned here, as well as other structures not shown, visible as well as possible to a person performing the treatment. Instead of a mono-energetic image such as the output images A, B, C, D, E, F, G, H shown here, a type of mixed image from measurement data based on different acquisition energies will be created, with the aid of which the detectability of structures can likewise be enhanced. The reader is referred in this connection to the optimum contrast method mentioned above.

FIG. 2 shows an example embodiment of an inventive method Z. Connected upstream from this method are two computed tomography image acquisitions 9, 11 of the same body of the patient P in the same acquisition area. These image acquisitions are undertaken with different energies. The result is first measurement data $MD_1$ from the first image acquisition 9 and second measurement data $MD_2$ from the second image acquisition 11. This measurement data $MD_1$, $MD_2$ is accepted in a first method step 13.

In a second method step 15 an optimized output ODA of target image points is then set. This is done based on the first and second measurement data $MD'$, $MD_2$ in each case at the target image points. This is based on local optimization parameter values OPW, which are defined in advance in a step 16 (upstream from the method, such as by presetting or obtained by a user). Taking into account these optimization parameter values OPW in relation to the target image points, which are each determined locally in the first and second measurement data $MD_1$, MD2 in the area of the target image points, this setting is thus made. In such cases, in a third method step 17 the image point reproduction parameter values BWP are derived in each case, which represent the optimized output ODA of the target image points. A fourth method step 19 is the determination 19 of output data DBD based on the optimized output ODA of the target image points.

These steps are explained by way of example on the basis of FIG. 3. For better understanding and as a reference an output image J of a patient P is shown here as a representation, on which specific image points $BP_1$, $BP_2$, $BP_3$, $BP_4$ are marked. The first image point $BP_1$ is localized here within the liver 3 of the patient P, the second image point $BP_2$ in the area of the fatty tissue 5, the third image point $BP_3$ in the area of the kidneys 5 and the fourth image point $BP_4$ in the area of the spinal column 1. These image points $BP_1$, $BP_2$, $BP_3$, $BP_4$ are each pixels $BP_1$, $BP_2$, $BP_3$, $BP_4$ of the output image J and at the same time correspond to a location in the body of the patient P.

The image points $BP_1$, $BP_2$, $BP_3$, $BP_4$ are each assigned an HU value curve, on which the signal strength at image point $BP_1$, $BP_2$, $BP_3$, $BP_4$ in HU is plotted against the energy in keV (i.e. the aforementioned energy during the acquisition or a given virtual energy derived from two acquisitions with different energies). These HU value curves are purely schematic and do not necessarily correspond to a measurable actual behavior at the respective image point $BP_1$, $BP_2$, $BP_3$, $BP_4$. It can be seen that at each image point $BP_1$, $BP_2$, $BP_3$, $BP_4$ a maximum of the HU value is reached at a different energy.

A similar method of operation might be possible for representing the contrast-noise ratio (CNR) via the energy, which is viewed below as a decisive optimization parameter:

On the basis of the HU value curves and similar CNR curves an HU value can be defined locally at the respective image point $BP_1$, $BP_2$, $BP_3$, $BP_4$: initially a local CNR is calculated for all energy levels for each image point $BP_1$, $BP_2$, $BP_3$, $BP_4$ and its immediate environment. The corresponding HU values are also determined in precisely the same way. Thus an HU value curve and a CNR curve are available. If optimization is now to be in accordance with the CNR as optimization parameter, the maximum of the CNR at the respective image point $BP_1$, $BP_2$, $BP_3$, $BP_4$ is sought and on the basis of the energy corresponding to this CNR maximum the corresponding HU value is selected. This HU value serves as a signal value at the image point $BP_1$, $BP_2$, $BP_3$, $BP_4$ concerned. This method of operation is carried out for each image point until the measurement data $MD_1$, $MD_2$ of an area under examination of the patient P has been fully processed.

FIG. 4 shows in a schematic block diagram an example embodiment of an inventive computed tomograph 21. It includes an acquisition unit 23 and an example embodiment of an inventive image data acquisition system 27.

The image data acquisition system 27 comprises an input interface 25, a setting and derivation unit 29, a determination unit 31 and an output interface 33. An inventive method Z now executes in the image data acquisition system 27, as has already been explained with the aid of FIG. 2:

The first and second measurement data $MD_1$, $MD_2$ arrive via the input interface 25 (which can also comprise two individual interfaces separated from one another functionally and/or spatially) in the image data acquisition system 27.

There in the setting and derivation unit 29 an optimized output ODA of target image points $BP_1$, $BP_2$, $BP_3$, $BP_4$ on the basis of the first and second measurement data in $MD_1$, $MD_2$ is determined as a function of the local optimization parameter values OPW of the target image points $BP_1$, $BP_2$, $BP_3$, $BP_4$, which are each determined locally from the first and second measurement data $MD_1$, $MD_2$ in the area of the target image points in $BP_1$, $BP_2$, $BP_3$, $BP_4$. The setting and derivation unit 29 also derives image point reproduction parameter values BWP, which represent the optimized output ODA of the target image points $BP_1$, $BP_2$, $BP_3$, $BP_4$. For these purposes the setting and derivation unit 29 can also be embodied as a number of components and especially have a setting subunit and a derivation subunit similar to steps 15 and 17 in FIG. 2.

The determination unit 31 determines the output data DBD based on the optimized output ODA of the target image points $BP_1$, $BP_2$, $BP_3$, $BP_4$. It thus derives the output data DBD from the specifications for optimized output ODA. This output data DBD is then passed on by the output interface 33 to a user and/or to other modalities and/or to a data memory.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the program of any of the above mentioned embodiments and/or to perform the method of any of the above mentioned embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Although the invention has been illustrated and described in detail on the basis of the preferred example embodiment, the invention is not limited by the disclosed examples and other variations can be derived herefrom by the person skilled in the art, without departing from the scope of protection of the invention.

In conclusion it is pointed out once again that the method described in detail above and the facilities presented merely involve example embodiments which can be modified by the person skilled in the art in a wide variety of ways without departing from the area of the invention. Thus the method is especially not only able to be used with two energies, but also for a creation of optimized output data with more than two energies, wherein operation can be both with a number of different constant energy levels and also with a number of variable energy levels. Furthermore the use of the indefinite article "a" or "an" does not preclude the features involved also being able to be present a number of times.

What is claimed is:

1. A method for automatically obtaining optimized output data from inside an examination object from images of a computed tomograph, comprising:
    accepting first measurement data of the examination object, acquired on the basis of x-ray radiation of a first energy, and second measurement data of the examination object, acquired on the basis of x-ray radiation of a second energy differing from the first energy;
    setting an optimized output of respective target image points based on the first and second measurement data at respective target image points as a function of respective local optimization parameter values of the respective target image points, each respectively determined locally from the first and second measurement data in the area of the target image points, while deriving image point reproduction parameter values, which each represent the optimized output of the respective target image points; and
    determining output data on the basis of the optimized output of the target image points.

2. The method of claim 1, wherein the optimization parameter values of the respective target image points include at least one of the following parameter values:
    contrast between a respective target image point and its immediate environment, image noise between the respective target image and its immediate environment, contrast-noise ratio between the respective target image point and its immediate environment, and
    output signal strength at the respective target image point.

3. The method of claim 2, wherein the contrast of the respective target image point in relation to its immediate environment or the contrast-noise ratio between the respective target image and its immediate environment or the output signal strength at the respective target image point will be regulated in to a maximum.

4. The method of claim 2, wherein the image noise at the respective target image point and its immediate environment will be regulated in to a minimum.

5. The method of claim 1, wherein the optimization parameter values of the respective target image points are determined as a function of a parameter value determination at the respective target image point and its immediate environment.

6. The method of claim 5, wherein the image point reproduction parameter values of the respective target image points are regulated in at the respective target image point and its immediate environment.

7. The method of claim 1, wherein the setting is executed for a number of directly adjacent target image points of the examination object.

8. The method of claim 1, wherein the setting is executed for all respective target image points within a previously defined representation area of the examination object.

9. The method of claim 1, wherein the respective image point reproduction parameter values are derived during the setting by the first and second measurement data at the respective target image point being blended with one another in a derived ratio present as a function of an optimization parameter value at the respective target image point.

10. The method of claim 1, wherein the respective image point reproduction parameter values are determined during the setting by calculating respective mono-energetic target image points on the basis of a third energy from the two measurement data items with reference to an assignment database.

11. The method of claim 1, wherein the respective image point reproduction parameter values are additionally derived as a function of knowledge interest-oriented parameter specifications for at least one of the examination object and a respective target region of the examination object.

12. The method of claim 11, wherein the parameter specifications are obtainable from a user.

13. The method of claim 2, wherein the optimization parameter values of the respective target image points are determined as a function of a parameter value determination at the respective target image point and its immediate environment.

14. The method of claim 13, wherein the image point reproduction parameter values of the respective target image points are regulated in at the respective target image point and its immediate environment.

15. A non-transitory computer readable medium including program code segments for, when executed on a programmable system, causing the programmable system to implement the method of claim 1.

16. A non-transitory computer readable medium including program code segments for, when executed on a programmable system, causing the programmable system to implement the method of claim 2.

17. A system for obtaining image data for automatically obtaining optimized output data from inside an examination object from images of a computed tomograph, comprising:

an input interface, configured to accept first measurement data of the examination object, acquired on the basis of x-ray radiation of a first energy, and second measurement data of the examination object, acquired on the basis of x-ray radiation of a second energy differing from the first energy;

a setting and derivation unit configured to, during operation, derive an optimized output of respective target image points on the basis of the first and second measurement data as a function of local optimization parameter values of the respective target image points, each respectively determined locally from the first and second measurement data in the area of respective the target image points, and configured to, during operation, derive image reproduction parameter values, which represent the optimized output of the respective target image points; and a determination unit, configured to determine the output data on the basis of the respective optimized output of the respective target image points.

18. A computed tomograph, comprising the system of claim 17, configured to obtain image data.

* * * * *